(12) United States Patent
Schneider et al.

(10) Patent No.: US 10,926,035 B2
(45) Date of Patent: Feb. 23, 2021

(54) CARTRIDGE HOLDER OF AN INJECTION DEVICE

(71) Applicant: SANOFI-AVENTIS DEUTSCHLAND GMBH, Frankfurt am Main (DE)

(72) Inventors: Christiane Schneider, Frankfurt am Main (DE); Martin Vitt, Frankfurt am Main (DE); Michael Joest, Obertshausen (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 557 days.

(21) Appl. No.: 15/558,325

(22) PCT Filed: Mar. 21, 2016

(86) PCT No.: PCT/EP2016/056103
§ 371 (c)(1),
(2) Date: Sep. 14, 2017

(87) PCT Pub. No.: WO2016/150898
PCT Pub. Date: Sep. 29, 2016

(65) Prior Publication Data
US 2018/0064877 A1 Mar. 8, 2018

(30) Foreign Application Priority Data

Mar. 23, 2015 (EP) .................................... 15160253

(51) Int. Cl.
*A61M 5/24* (2006.01)
*A61M 5/315* (2006.01)
(Continued)

(52) U.S. Cl.
CPC ............ *A61M 5/2455* (2013.01); *A61M 5/24* (2013.01); *A61M 5/31551* (2013.01);
(Continued)

(58) Field of Classification Search
CPC ........ A61M 5/2455; A61M 2005/2407; A61M 2005/2418; A61M 2005/2477;
(Continued)

(56) References Cited

U.S. PATENT DOCUMENTS 2,672,868 A 3/1954 Hickey
5,358,489 A 10/1994 Wyrick
(Continued)

FOREIGN PATENT DOCUMENTS

CH 707217 4/2014
JP 2005-531348 10/2005
(Continued)

OTHER PUBLICATIONS

International Preliminary Report on Patentability in International Application No. PCT/EP2016/056103, dated Sep. 26, 2017, 6 pages.

(Continued)

*Primary Examiner* — Theodore J Stigell
(74) *Attorney, Agent, or Firm* — Fish & Richardson P.C.

(57) ABSTRACT

The present disclosure relates to a cartridge holder of an injection device, the cartridge holder comprising a tubular shaped elongated sleeve extending in an axial direction to accommodate a cartridge filled with a medicament, wherein the sleeve (29) comprises:
- a proximal connecting end to connect with a distal connecting end of a body of the injection device, which body is configured to accommodate a drive mechanism of the injection device and which drive mechanism is operably engageable with a piston of the cartridge,
- a flange section extending radially outwardly from an outside surface of the sleeve and having a proximally facing abutment face to axially abut with a distal end face of the distal connecting end of the body, (Continued)

at least three protrusions located distally from the flange section, extending radially outwardly from the outside surface of the sleeve and being distributed around the circumference of the sleeve.

14 Claims, 5 Drawing Sheets

(51) Int. Cl.
*A61M 5/32* (2006.01)
*A61M 5/34* (2006.01)

(52) U.S. Cl.
CPC .......... *A61M 5/3202* (2013.01); *A61M 5/347* (2013.01); *A61M 2005/2407* (2013.01); *A61M 2005/2418* (2013.01); *A61M 2005/2477* (2013.01); *A61M 2005/2492* (2013.01)

(58) Field of Classification Search
CPC .......... A61M 2005/2492; A61M 5/347; A61M 5/24; A61M 5/31551; A61M 5/3202
See application file for complete search history.

(56) References Cited

U.S. PATENT DOCUMENTS

| | | | |
|---|---|---|---|
| 5,593,391 A | 1/1997 | Stanners | |
| 10,569,025 B2* | 2/2020 | Tschirren | .......... A61M 5/31541 |
| 2005/0288607 A1 | 12/2005 | Konrad | |
| 2012/0089097 A1* | 4/2012 | Harms | .................... A61M 5/24 |
| | | | 604/187 |
| 2012/0283649 A1* | 11/2012 | Veasey | .............. A61M 5/31555 |
| | | | 604/208 |
| 2013/0072879 A1* | 3/2013 | Avery | .................... A61M 5/24 |
| | | | 604/189 |
| 2013/0253433 A1* | 9/2013 | Senior | .................... A61M 5/31 |
| | | | 604/187 |
| 2017/0348489 A1* | 12/2017 | Hirschel | ................ A61M 5/24 |

FOREIGN PATENT DOCUMENTS

| | | | |
|---|---|---|---|
| JP | 2015-500125 | | 1/2015 |
| WO | WO 2004/002556 | | 1/2004 |
| WO | WO 2004/078239 | | 9/2004 |
| WO | WO 2004/078240 | | 9/2004 |
| WO | WO 2004/078241 | | 9/2004 |
| WO | WO-2010/147553 | * | 12/2010 |
| WO | WO 2010/147553 | | 12/2010 |
| WO | WO 2013/089620 | | 6/2013 |
| WO | WO-2014/056874 | * | 4/2014 |
| WO | WO 2014/056874 | | 4/2014 |

OTHER PUBLICATIONS

International Search Report and Written Opinion in International Application No. PCT/EP2016/056103, dated May 11, 2016, 8 pages.

* cited by examiner

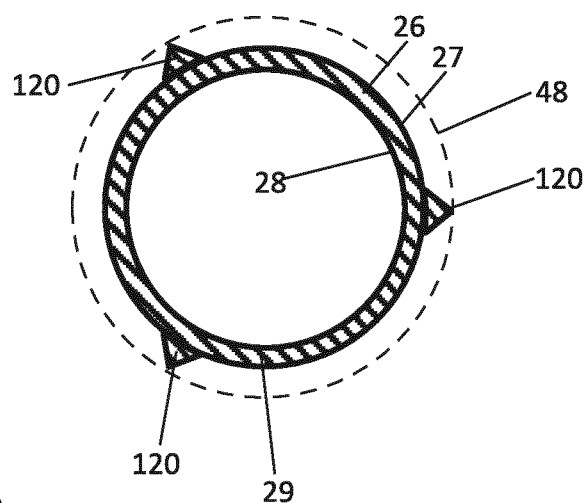
Fig. 2
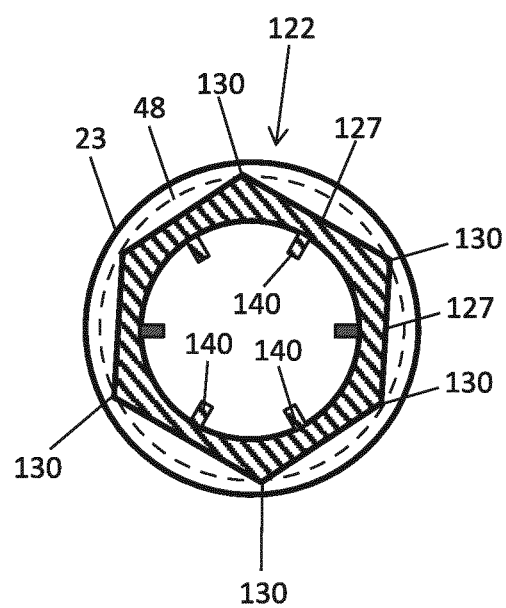
Fig. 3  A-A
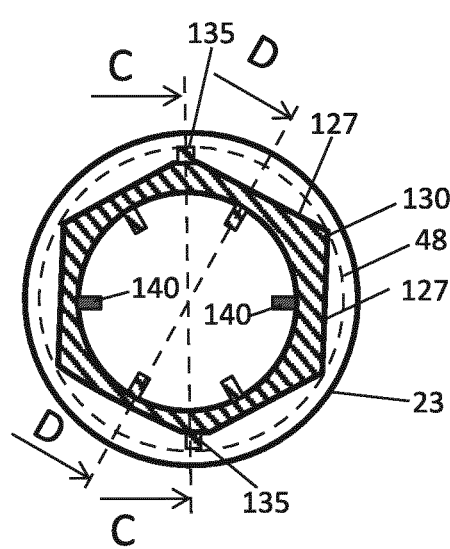
Fig. 4  B-B

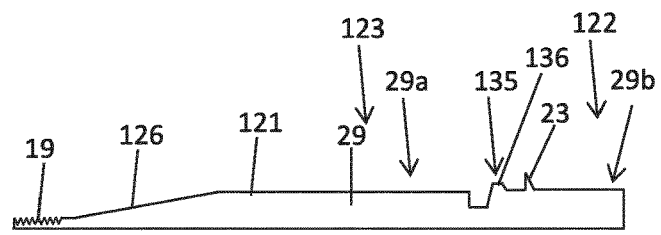
Fig. 5   C-C
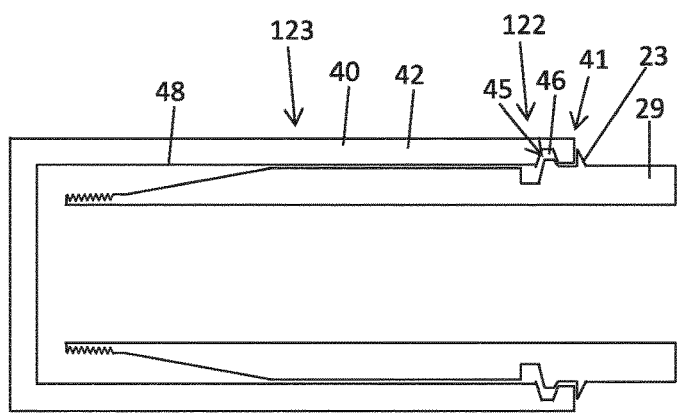
Fig. 6
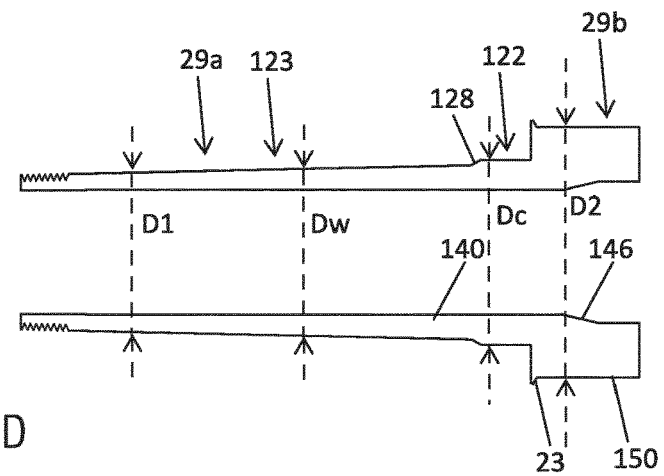
Fig. 7   D-D
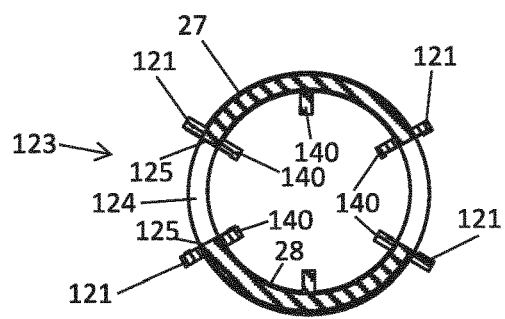
Fig. 8   E-E

CARTRIDGE HOLDER OF AN INJECTION DEVICE

CROSS REFERENCE TO RELATED APPLICATIONS

The present application is the national stage entry of International Patent Application No. PCT/EP2016/056103, filed on Mar. 21, 2016, and claims priority to Application No. EP 15160253.9, filed in on Mar. 23, 2015, the disclosures of which are expressly incorporated herein in entirety by reference thereto.

TECHNICAL FIELD

The present disclosure relates in one aspect to a cartridge holder of an injection device, such like a pen-type injector operable for setting and dispensing of a dose of a medicament. In particular, the disclosure relates to a cartridge holder to retain and to fix a cartridge filled with a liquid medicament, which cartridge is of reduced diameter compared to standard sized cartridges conventionally used with pen-type injection devices. In another aspect the disclosure relates to an injection device equipped with such a cartridge holder.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Existing and commercially distributed pen-injectors may be equipped with cartridges providing a predefined volume for a liquid medicament, e.g. 3 ml. The injection devices are typically configured to provide user-operated variable setting of a dose and subsequent dispensing or delivery thereof. Typically, a dose can be selected and dispensed in discreet steps of e.g. one or several International Units (IU). Most injection devices on the market are configured and designed for use of grown up patients.

In the field of pediatric treatment it is desirable to reduce the dose of medicaments and to administer non-integer amounts of IU to a patient. This requires smaller dose increments to be selectable. It is therefore desirable to set and to dispense doses having a size of less than one IU, e.g. of half units. Hence, it is desirable to provide dose setting with increments of half units or less in order to increase dosing accuracy and to allow for a finely segmented, precise setting and dispensing of doses of a particularly small size.

In order to meet these requirements existing injection devices require modifications.

It is therefore an object of the present disclosure to provide a rather simple approach to enable setting and dispensing of doses of reduced size, in particular to provide setting and dispensing of half units or other non-integer units of a liquid medicament by making use of an existing drive mechanism of an injection device. The present disclosure should provide modifications to an existing injection device, which modifications are simple and cost efficient to realize.

SUMMARY

In a first aspect the disclosure relates to a cartridge holder of an injection device, wherein the cartridge holder comprises a tubular-shaped elongated sleeve extending in an axial direction to accommodate a cartridge filled with a medicament. It is of particular advantage that the cartridge is reduced in size compared to standard sized cartridges conventionally used with this type of injection device. In particular, the cartridge holder typically comprising a tubular-shaped sleeve is at least in sections reduced in diameter compared to standard sized cartridge holders configured to house standard sized cartridges. In this way, a conventional drive mechanism providing a well-defined advancing of a piston rod operably engageable with a piston of a cartridge can be used.

By means of the diameter reduction of the cartridge a reduced volume of the liquid medicament can dispensed by a well-defined distally directed displacement of the piston rod of the injection device. Hence, by replacing a standard sized cartridge, e.g. providing a filling volume of 3 ml, by a size reduced and/or diameter reduced cartridge the relation of a dispensed volume per distally directed displacement of the injection device's piston rod can be reduced by a factor or ratio R that is governed by the modified geometry of the cartridge.

The reduction of the diameter of the cartridge also requires particular modifications to the cartridge holder configured to accommodate and to fix such a modified cartridge inside the housing of the injection device.

The sleeve of the cartridge holder comprises a proximal connecting end to connect with a distal connecting end of a body of the injection device. The body is configured to accommodate the drive mechanism of the injection device. The drive mechanism is operably engageable with a piston of the cartridge, which cartridge can be accommodated and positionally fixed inside the sleeve of the cartridge holder.

The sleeve of the cartridge holder further comprises a flange section extending radially outwardly from an outside surface of the sleeve. The flange section has a proximally facing abutment face to axially abut with a distal end face of the distal connecting end of the body. In a final assembly or in a fastening position of cartridge holder and body the abutment face of the flange section is in axial abutment with the distal end face of the body. Typically, the flange section is of substantially annular shape and extends all around the outer circumference of the sleeve of the cartridge holder.

The sleeve further comprises at least three protrusions located distally from the flange section. The at least three protrusions extend radially outwardly from the outside surface of the sleeve. Furthermore, the at least three protrusions are distributed around the circumference of the sleeve. The at least three protrusions serve as a guiding structure and as a support structure for a protective cap configured to cover the cartridge holder and hence to protect the distal end of the injection device. By means of the at least three protrusions, the overall diameter of the sleeve can be reduced in order to adapt the shape and geometry of the cartridge holder closer to the diameter-reduced shape and geometry of the cartridge to be positioned therein.

The at least three protrusions may be equidistantly or equiangularly spaced about the outer circumference of the sleeve. But it is also conceivable that the circumferential distance between neighboring or adjacently located protrusions varies and is therefore somewhat irregular.

By means of the at least three protrusions a conventional cap typically used and typically engageable with a conventional or standard sized cartridge holder can still be used. By means of the at least three protrusions any reduction of the outer diameter of the cartridge holder can be compensated.

According to another embodiment a distal portion of the sleeve located distally from the flange section comprises an outer diameter that is smaller than an outer diameter of a proximal portion of the sleeve located proximally from the flange section. The flange section typically comprising an annular flange extending along the entire circumference of the sleeve divides the sleeve in axial direction into the distal portion and the proximal portion. The proximal portion of the sleeve, i.e. the portion of the sleeve that is located proximally from the flange section is typically configured to be inserted into a receptacle of the body located at a distal end of the body. In this way, the cartridge holder and the body of the injection device can be mutually connected and fixed in a radially overlapping way. The proximal portion of the sleeve may be completely insertable into the receptacle of the distal connecting end of the cartridge holder so that the proximal connecting end of the cartridge holder and the distal connecting end of the body are fixed and connected in a nested or interleaved way.

By reducing the outer and the inner diameter of the distal portion of the sleeve of the cartridge holder a diameter-reduced and hence size reduced cartridge can be fixed and accommodated therein. The larger outer diameter of the proximal portion compared to the distal portion of the sleeve then allows and enables a connection of the cartridge holder with a conventional or with an existing body of the injection device, which body is universally connectable with a standard sized or reference cartridge holder and with a size- or diameter-reduced cartridge holder according to the present disclosure.

In order to make use of a diameter-reduced cartridge only the cartridge holder geometry and the cartridge holder design has to be modified. By leaving the proximal portion of the sleeve substantially unchanged a connection of the body with a geometrically modified cartridge holder can remain substantially unchanged.

Any variations of the outer diameter of the distal portion of the sleeve compared to the proximal portion may be effectively compensated by the at least three protrusions. In this way also the design and geometry of the protective cap may remain unchanged.

According to another embodiment the distal portion of the sleeve comprises a cap engaging section and a window section, wherein the cap engaging section is axially located between the window section and the flange section. In other words, the window section is located distally from the cap engaging section. The cap engaging section forms a proximal end of the distal portion of the sleeve. The cap engaging section comprises at least one or more fastening elements to provide a releasable fastening of the cap to the cartridge holder. Typically, mutually corresponding fastening elements of the cap engaging section and of the cap to cover the entire cartridge holder are configured as a positive interlock, e.g. as a snap fit or snap engagement.

The window section is located distally from the cap engaging section. The window section may be located directly adjacent to the cap engaging section and may hence adjoin the cap engaging section.

Typically, the window section is transparent at least in sections so as to provide visual inspection of the cartridge accommodated therein. The window section may comprise a somewhat tubular shape. In distal direction the window section of the sleeve may adjoin a threaded socket of the sleeve by way of which a correspondingly threaded needle assembly can be releasably attached to the cartridge holder.

According to another embodiment the cap engaging section comprises an outer diameter that is larger than an outer diameter of the window section. A radially widened cap engaging section is of particular benefit to establish and to provide a well-defined mutual fastening of the cartridge holder and the protective cap. The cap engaging section may further provide an axial guiding of the cap when placing the cap onto the cartridge holder in proximal direction. By means of the radially widened cap engaging section a rather slack free or clearance free positive engagement or frictional engagement between the sleeve and the protective cap can be obtained.

Typically, the outer diameter or the outer shape of the cap engaging section is adapted and configured to match with an inside facing sidewall structure at a proximal end of the protective cap. By reducing the outer diameter of the window section compared to the outer diameter of the cap engaging section the thickness of a sidewall of the window section can be reduced compared to the cap engaging section. In this way material and weight can be saved for the manufacturing of the sleeve of the cartridge holder. A reduced wall thickness is also beneficial to obtain accurate and dimensionally stable geometries of the sleeve when manufactured by way of injection molding. Inevitable shrinking of the plastic material will then only have a lower impact on the geometric tolerances of the sleeve.

Moreover, a reduction of the wall thickness of the sleeve in the region of the window section compared to the cap engaging section is beneficial in regard to inevitable absorption of electromagnetic radiation in the visible spectrum, hence in regard to the absorption of visually perceptible light. A comparatively thin sidewall in the region of the window section provides a good visual inspection of a cartridge located inside the cartridge holder. Moreover, a filling level of a transparent medicament can be better determined when the thickness of a transparent sidewall of the window section is below a predetermined thickness.

Making use of a radially thickened cap engaging section compared to the window section is further beneficial in terms of transferring mechanical loads between the protective cap, the cartridge holder and the body. Since the distally located window section of the sleeve only serves to keep the cartridge located therein in a fixed and well-defined position it is to be assumed that mechanical loads on the window section are generally smaller than in the cap engaging section located directly adjacent to the interface of cartridge holder and body. It is therefore beneficial to reduce the outer diameter of the window section compared to the outer diameter of the cap engaging section to save material and weight and to provide a tight and secure fixing of a cartridge inside the cartridge holder.

According to another embodiment the window section of the sleeve comprises at least one through opening in a sidewall of the sleeve. Typically, the at least one through opening extends in longitudinal or axial direction. It may be of rectangular shape, wherein the rectangular-shaped window section has an axial length that exceeds its circumferential width. Typically, the axial length of the through opening is 5 to 15 times larger than the circumferential width of the through opening. By means of a through opening an even better visual inspection of a cartridge located inside the cartridge holder can be provided. Furthermore, when providing at least one or even two circumferentially oppositely and radially overlapping through openings in the sidewall of the sleeve the sleeve does not necessarily have to be made of a transparent material.

According to another embodiment the sleeve comprises at least three axially extending inner ribs protruding radially inwardly from an inside surface of the sleeve. Typically, the inner ribs protrude radially inwardly from a sidewall of the sleeve. Furthermore, they are distributed around the inner circumference of the sleeve. It is of particular benefit, when the inner ribs are equidistantly or equiangularly distributed or spaced about the inner circumference of the sleeve. The at least three inner ribs may extend substantially parallel in axial direction. They may extend across the flange section. Hence, a proximal end of the inner ribs may be located in the proximal portion of the sleeve while a distal end of the inner ribs may be located in the distal portion of the sleeve.

By means of the at least three axially extending inner ribs the flexural strength and mechanical stability of the sleeve can be improved. In addition, the inner ribs may provide radial support for the outer circumference of the tubular-shaped cartridge when arranged inside the cartridge holder. In this way the inner ribs effectively act and serve as a radial support structure for the cartridge. Moreover, by means of radially inwardly extending ribs a difference in the outer shape or outer diameter of the proximal portion and the distal portion of the sleeve can be effectively reduced. In this way, the difference of the diameter between a standard cartridge and a diameter-reduced cartridge can be compensated by the radial extension of the inner ribs and by the difference in the diameters of the proximal portion and the distal portion of the sleeve.

Typically, there are provided even more than just three axially extending inner ribs. For instance, there may be provided four, five, six, seven, eight or even more inner ribs typically equally spaced in circumferential direction to provide a multiple radial support for the cartridge positioned inside the cartridge holder.

Inner ribs or a constantly reducing inner diameter of the sleeve in distal direction further serves to axially guide and to align the cartridge inside the cartridge holder. In this way a well-defined axial guiding and a rather precise alignment of the cartridge along the longitudinal axis of the cartridge holder can be obtained. For a smooth distally directed and repeated displacement of the piston rod in the course of subsequent dose delivery procedures it is of particular benefit when the barrel of the cartridge almost exactly co-aligns with the longitudinal extend of the piston rod. In this way a strain of buckling loads to the piston can be effectively reduced and frictional forces between the piston and the side wall of the barrel of the cartridge can be kept substantially constant over the entire displacement path of the piston inside the barrel.

According to another embodiment at least one of the inner ribs extends along a lateral side edge of the at least one through opening of the window section. Typically, the lateral edge of the through opening extends in axial direction. It co-aligns and coincides with at least one of the inner ribs. In this way the at least one inner rib serves to mechanically stabilize and to mechanically strengthen the window section of the sleeve in direct vicinity of the through opening. Any through opening in the sidewall of the sleeve represents a mechanical weakening or a structurally vulnerable portion. By arranging at least one of the inner ribs along a lateral side edge of the through opening the structural weakening inherently induced by the through opening can be counteracted or at least partially compensated.

It is of particular benefit, when both oppositely located lateral side edges of the through opening are each provided with an inner rib. In this way, both lateral side edges are structurally strengthened and may be less susceptible to mechanical loads or damage.

According to another embodiment at least one of the protrusions comprises an elongated and axially extending outer rib on the outside surface of the distal portion of the sleeve. By means of axially extending outer ribs a kind of a supporting and guiding structure for the protective cap can be provided. By means of at least three axially extending outer ribs on the distal portion of the sleeve a radial support for the inside facing sidewall portion of a cup-shaped protective cap is provided.

Typically, there are provided at least three elongated axially extending outer ribs on the outside surface of the distal portion of the sleeve. At least one of these outer ribs may adjoin axially to the cap engaging section, thereby providing a smooth guiding of e.g. the protective cap towards the cap engaging section. The outer ribs further enhance and improve mechanical stability and the rigidity of the sleeve.

It may be of further benefit that outer ribs of the window section are exclusively provided at lateral side edges of the at least one through opening. In this way, residual portions of the outside surface of the window section of the sleeve could be provided with a rather smooth or cylindrically-shaped structure that would be beneficial for printing or for adhering a label to the outside surface of the sidewall of the cartridge holder tangentially between two adjacently located outer ribs.

Typically, there are provided at least three or even more outer ribs. There may be provided four, five, six, seven, eight or even more outer ribs that may be either equidistantly or equiangularly distributed or spaced about the outer circumference of the sleeve, in particular of its window section. But it is even conceivable that the angular position of the outer ribs is somewhat irregular.

In a further embodiment at least one of the outer ribs extends along a lateral side edge of the at least one through opening of the window section. An outer rib along a lateral side edge of the at least one through opening may be provided instead or alternative to an inner rib extending along the same or another lateral side edge of the through opening. However, it is even conceivable that at least one lateral side edge of the through opening provided in the window section is provided with an outer rib and with an inner rib. One lateral side edge of the through opening may coincide with an outer rib and another lateral side edge thereof may coincide with an inner rib. However, it is also conceivable, that both lateral side edges of the at least one through opening in the sidewall of the sleeve is provided with both, an inner rib and with an outer rib. In this way, the mechanical stability and rigidity of the window section of the sleeve can be further enhanced.

According to another embodiment at least one of the inner ribs comprises a beveled proximal end. Typically, all inner ribs comprise a beveled proximal end. In this way, a distally directed insertion of a tubular-shaped cartridge into the cartridge holder from a proximal end thereof can be facilitated and improved. By means of a beveled proximal end the inner ribs provide a radial guiding of the cartridge during an insertion of the cartridge into the cartridge holder.

Alternative or in addition at least one of the outer ribs also comprises a beveled distal end. Typically, all outer ribs comprise a beveled distal end. In this way the outer ribs also provide a radial guiding of the protective cap when placed over the cartridge holder. By means of such a radial guiding the protective cap can be precisely radially positioned relative to the cartridge holder in the course of inserting the cartridge holder into the protective cap so that mutually corresponding fastening elements of the cartridge holder and the protective cap are correctly radially positioned before they engage. A beveled distal end of the outer ribs may be also beneficial to match with the shape of a protective cap exhibiting a convex or generally narrowing shape near or towards its distal end.

According to another embodiment the cap engaging section of the distal portion of the sleeve comprises at least two fastening elements to releasably engage with at least one complementary-shaped fastening structure of a cap that is configured to cover the sleeve. Typically, the fastening elements are located on circumferential opposite portions on the outside surface of the cap engaging section. Instead of two fastening elements it is also conceivable to make use of three or even more fastening elements distributed or spaced about the outer circumference of the cap engaging section. Typically, the fastening elements are equidistantly or equiangularly spaced about the outer circumference of the cap engaging section.

The fastening elements provided on the cap engaging section are typically implemented as radially outwardly extending protrusions to positively engage with a complementary-shaped recess on an inside surface of the protective cap. Typically, the cap is exclusively axially engageable with the at least two fastening elements of the cap engaging section. In this way, the cap may be rotated with regard to its longitudinal axis while being fixed to the cartridge holder. In order to provide such a rotation-invariant fixing of the protective cap and the cartridge holder it is of particular benefit, when the cap comprises a radial groove at the inside surface of its sidewall to engage with the at least two radially outwardly protruding fastening elements. The cap and/or the fastening elements are elastically deformable or elastically pivotable so as to provide a releasable engagement of the protective cap with the cap engaging section.

In another embodiment the cap engaging section also comprises at least three radially outwardly extending protrusions adjoining the flange section in axial direction. The at least three protrusions are distributed around the circumference of the cap engaging section. Making use of these protrusions in the cap engaging section helps to radially align the cap and its fastening structure to the fastening elements provided on the outer circumference of the cap engaging section. Typically, the radially outwardly located ends of the outwardly extending protrusions of the cap engaging section match with the inner diameter of the cap so that the protective cap is radially supported by the at least three protrusions of the cap engaging section substantially free of clearance. This provides a well-defined and structurally stable connection of the protective cap and the cartridge holder.

Typically, the radially outwardly extending protrusions of the cap engaging section are beveled in distal direction so as to enable a smooth engagement of the protective cap with the protrusions of the cap engaging section of the cartridge holder.

In a further embodiment the cap engaging section comprises a polygonal-shaped outer cross-section. For instance, the cap engaging section may comprise a triangular, a quadratic, a rectangular, a pentagonal or hexagonal cross-section with substantially straight-shaped sections or lateral side surfaces and with respective corners. Irrespective on the choice of a particular polygonal shape the radially outwardly extending protrusions of the cap engaging section are located in the corners of a respective polygon. It is particularly conceivable that the corners of a polygon, e.g. the corners of a hexagonal-shaped cross-section of the cap engaging section just define or constitute the radially outwardly extending protrusions that are configured to radially support an inside surface of the protective cap when assembled onto the cartridge holder.

The polygonal-shaped cap engaging section does not necessarily have to be of regular polygonal shape. It is in particular conceivable that the fastening elements of the cap engaging section are located on a radially flattened side of the polygonal-shaped cap engaging section whereas residual corners or edges of the polygonal-shaped outer cross-section form radially outwardly extending protrusions to radially engage and to radially support the protective cap. A well defined polygonal-shaped outer surface of the cap engaging section is not only beneficial for an axial and radial guiding of the cap but is of further benefit in the course of an automated assembly of the injection device. The well-defined polygonal shaped cap engaging section may be easily gripped by fixing tools to hold, to transport and to assembly the cartridge holder to the body. Hence, the polygonal outer surface provides a kind of a keyed profile to match with a wrench type fastening, gripping or fixing tool.

According to another aspect the disclosure also relates to a cartridge holder assembly comprising a cartridge holder as described above and further comprising a cap, in particular a protective cap to cover at least a portion of the sleeve of the cartridge holder. Typically, the cap is configured to cover the entirety of the distal portion of the cartridge holder axially protruding from the body of the injection device when fully assembled. Radially outwardly located ends of the protrusions of the sleeve match with an inner diameter or with an inside surface of the cap. In this way the protrusions either implemented as rather axially confined or punctual protrusions in the cap engaging section of the sleeve or implemented as outer ribs on the window section of the sleeve are configured and shaped so as to provide radial abutment for the sidewall of the protective cap.

In another aspect the disclosure further relates to an injection device, in particular to a pen-type injector for administering a liquid medicament. The injection device comprises a cartridge holder as described above actually accommodating a cartridge filled with a liquid medicament, wherein the cartridge comprises a piston acting as a proximal seal, which piston is axially displaceably arranged inside a tubular-shaped barrel of the cartridge. In addition, the injection device also comprises a body connected to the cartridge holder and actually accommodating a drive mechanism operably engageable or being actually operably engaged with the piston of the cartridge.

Typically, the injection device is configured as a disposable injection device, wherein the cartridge holder is irreleasably connected to the body. Replacement of the cartridge is then not possible and would require destroying of at least one of the housing components, cartridge holder or body. Alternatively, the injection device could also be implemented as a re-usable device, wherein the cartridge holder is releasably connected to the body of the injection device.

With a reusable type of device an empty cartridge could be replaced by a new one and after a reset of the drive mechanism a connection of cartridge holder and body could be re-established.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, an embodiment of the disclosure is described in detail by making reference to the drawings, in which:

FIG. 2 shows a schematic transverse cross-section through the cartridge holder according to the present disclosure, FIG. 3 shows a cross-section through the cartridge holder along A-A according to FIG. 1, FIG. 4 is another transverse cross-section through the cartridge holder according to FIG. 1 along B-B, FIG. 5 is a longitudinal schematic cross-section through the cartridge holder along C-C according to FIG. 4, FIG. 6 is a schematic illustration of a protective cap fixed to the cartridge holder, according to FIG. 5, FIG. 7 is another longitudinal cross-section through the cartridge holder according to FIG. 4 along D-D, FIG. 8 is a transverse cross-section through the cartridge holder as shown in FIG. 9 along E-E.

DETAILED DESCRIPTION

Figure 1:
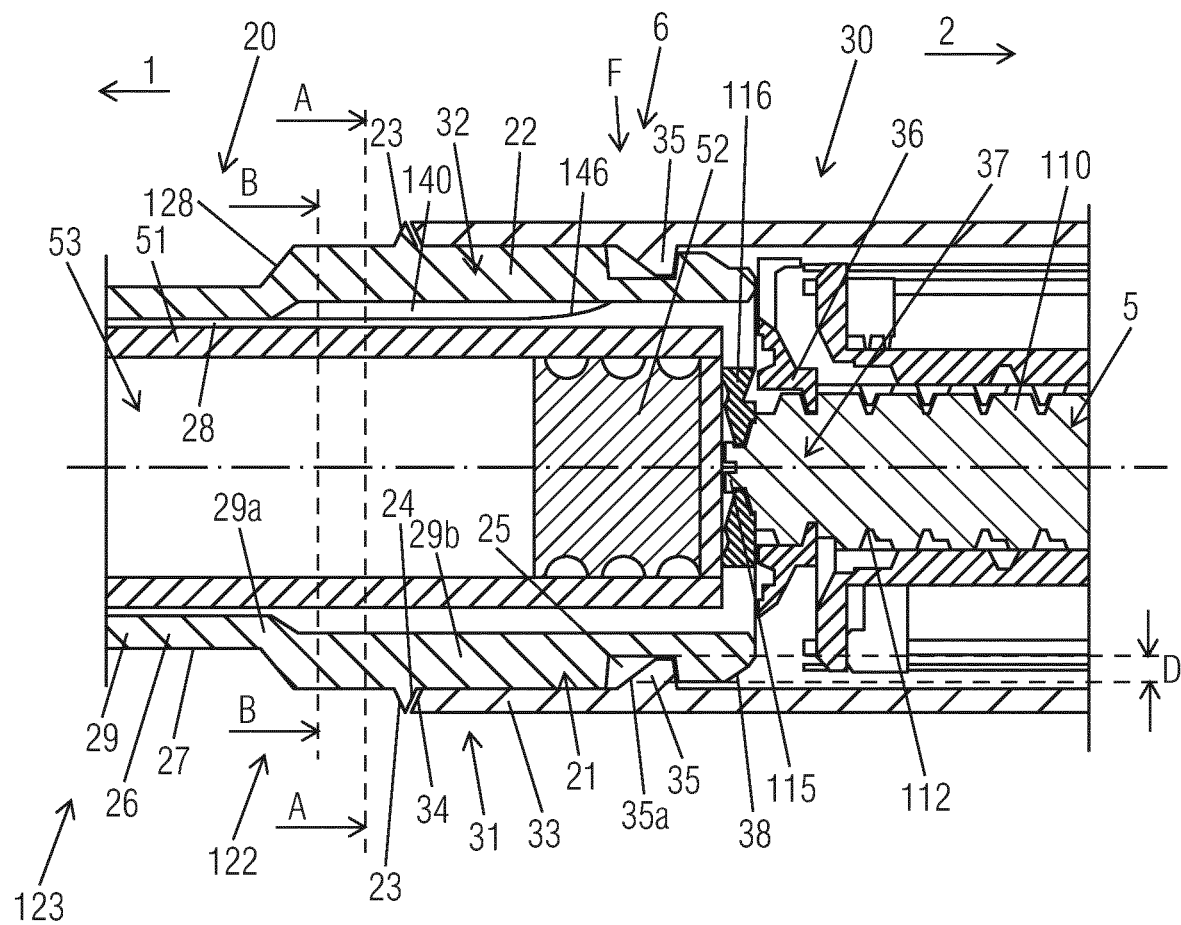
FIG. 1 is a longitudinal cross-section through the interface of a cartridge holder connected to a body of an injection device according to the present disclosure.
Figure 11:
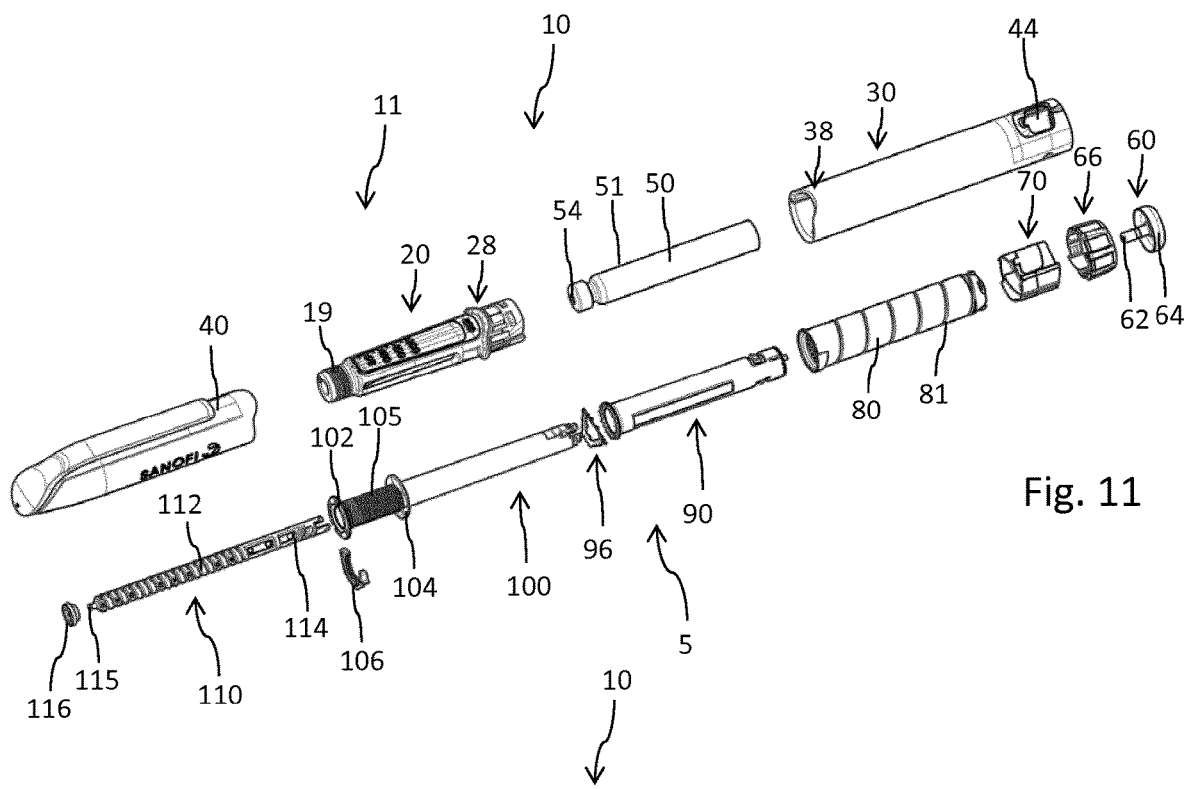
FIG. 11 is an exploded view of the components of one embodiment of an injection device comprising a cartridge holder as shown in FIGS. 1-10 and FIG. 12 is a longitudinal cross-section through the injection device according to FIG. 11 in a final assembly configuration.
Figure 12:
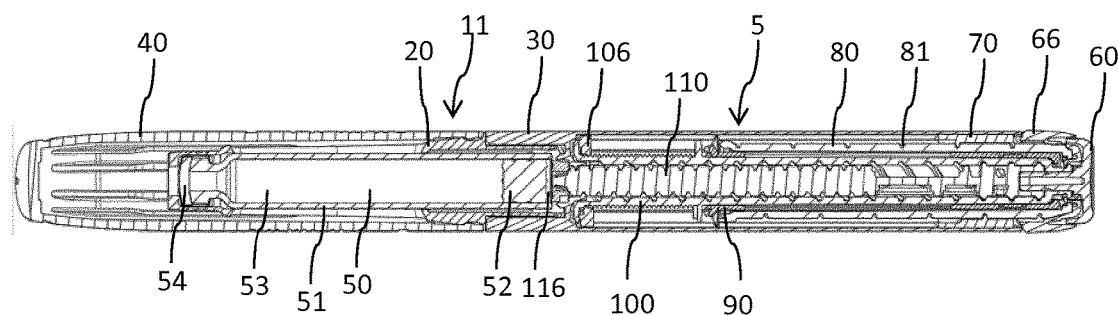

The injection device 10 as shown in FIGS. 1, 11 and 12 is configured as a pen-type injector. It comprises an elongated housing 11 extending in a longitudinal or axial direction. Towards a distal direction 1 the injection device 10 comprises a distal housing component denoted as cartridge holder 20. In the opposite longitudinal direction the housing 11 comprises a second housing component denoted as body 30. Both housing components, namely cartridge holder 20 and body 30 are of tubular and elongated shape. The cartridge holder 20 is configured to accommodate a cartridge 50 comprising a tubular-shaped barrel 51 and being filled with a liquid medicament 53. At a distal end the cartridge 50 comprises a pierceable seal 54 typically comprising a pierceable septum of an elastomeric material.

At the opposite proximal end the cartridge 50 is sealed by a piston 52 slidably arranged inside the barrel 51 of the cartridge 50. For dispensing of a dose of the liquid medicament 53 the cartridge holder 20 comprises a threaded socket 19 at its distal end to receive a correspondingly threaded needle assembly with a double-tipped injection needle. A proximal tipped end of the injection needle of the needle assembly, which is presently not illustrated, is configured to pierce the distal seal 54 of the cartridge 50 thereby gaining access to the interior of the cartridge 50. The distal end of the injection needle is then configured to puncture biological tissue to deliver the medicament. For medicament delivery the piston 52 is to be displaced in distal direction 1 under the action of a distally advancing piston rod 110 of a drive mechanism 5 of the injection device 10. The drive mechanism 5 is accommodated and fixed in the body 30 of the injection device 10.

The cartridge holder 20 and the body 30 are to be interconnected by means of a positive connection as it is explicitly shown in FIG. 1. The cartridge holder 20 comprises a proximal connecting end 21 to irreleasably interconnect with a distal connecting end 31 of the body 30. The cartridge holder 20 and the body 30 are interconnectable in an interleaved or nested way.

In the presently illustrated embodiment the proximal connecting end 21 of the cartridge holder 20 comprises an insert section 22 axially confined in distal direction 1 by a radially outwardly extending flange section 23. The distal connecting end 31 of the body 30 comprises a receptacle 32 to axially receive the insert section 22 of the cartridge holder 20. The outer diameter of the insert section 22 exactly matches with the inner diameter of the receptacle 32 so that the insert section 22 can be inserted into the receptacle 32 by means of a sliding motion in proximal direction 2 relative to the body 30.

The sidewall 33 of the receptacle 32 comprises a beveled axial end face 34 that forms a distal end of the body 30. The flange section 23 comprises a complementary-shaped beveled abutment face 24 featuring a geometric shape that matches with the shape of the beveled axial end face 34 of the sidewall 33. As it is shown in FIG. 1 the beveled abutment face 24 faces in proximal direction 2 whereas the beveled axial end face 34 faces in distal direction 1.

In order to irreleasably interconnect the cartridge holder 20 and the body 30 in a final assembly or final fastening position F there are provided mutually corresponding fastening elements 35 and 25 on the inside of the receptacle 32 and on the outside of the insert section 22. The body 30 comprises numerous fastening elements 35 radially inwardly extending from the inside of the sidewall 33 of the receptacle 32. The fastening elements are configured as snap features or snap protrusions extending radially inwardly from the sidewall 33 of the receptacle 32.

There are provided several e.g. four fastening elements 35 arranged along the inner circumference of the sidewall 33 of the receptacle 32. The fastening elements 35 are arranged near a flange-like threaded support 36 having a central through opening 37 through which the threaded piston rod 110 extends. The support 36 extends substantially perpendicular to the axial direction and confines the receptacle 32 in proximal direction 2. The support 36 effectively divides the body 30 into a distal interface section formed by the receptacle 32 and a proximal section to accommodate the mechanical components of the drive mechanism 5.

The fastening elements 35 provided on the inside of the sidewall 33 of the receptacle 32 comprise radially inwardly extending protrusions having a beveled section 35a facing in distal direction 1 and extending radially inwardly from the sidewall 33 to the crest of the protruding fastening element 35 to axially abut with a complementary shaped recessed fastening element 25 of the cartridge holder 20. The fastening element 25 comprises a radially extending recessed portion terminated in proximal direction 2 by a radially extending abutment section to axially abut with the fastening element 35. When the cartridge holder 20 and the body 30 are arranged in a final assembly configuration or fastening position F an axial interlock 6 between the fastening elements 25, 35 and hence between the cartridge holder 20 and the body 30 is established.

The proximal end of the cartridge holder 20 comprises a beveled edge 38 at its outer circumference that engages with the beveled section 35a of the protrusion 35 as the insert section 22 is urged in proximal direction 2 into the receptacle 32. The beveled edge 38 is at least located in an angular position on the proximal end of the insert section 22, that matches with an angular position of the respective fastening element 25. The beveled edge facilitates mutual assembly and induces an elastic deformation of both, the sidewall 33 of the receptacle 32 and of the insert section 22. The mutually corresponding fastening elements 25, 35 of cartridge holder 20 and body 30 are subject to tensile stress and to compressive stress during insertion of the insert section 22 into the receptacle 32, respectively.

Since the outer diameter of the insert section 22 matches with the inner diameter of the receptacle 32 an insert and fastening procedure requires elastic deformation of the housing component's cartridge holder 20 and body 30 due to the shape of the mutually corresponding fastening elements 25, 35. The housing components, cartridge holder 20 and body 30 are typically single pieced and are made by way of injection molding of a thermoplastic material.

During mutual assembly, the receptacle 32 and its sidewall 33 experiences a radially outwardly directed load or stress leading to tensile forces in circumferential direction inside the sidewall 33. Correspondingly, the insert section 22 experiences a radially inwardly directed pressure leading to compressive stress in circumferential direction inside the insert section 22. Since thermoplastic materials are more sensitive to tensile than to compressive stress it is of particular benefit, that weakening recessed structures are provided in the insert section of the cartridge holder 20. The radially inwardly extending protrusions of the fastening elements 35 of the body provide a structural reinforcement so that the sidewall 33 in the region of the fastening elements 35 is less susceptible in response to tensile loads that may arise during an assembly procedure.

The recessed fastening elements 25 provided in the insert section 22 of the cartridge holder 20 are configured as blind holes or pocket holes and do not completely intersect the wall structure of the insert section 22. Hence, a radial depth D of the recesses 25 is smaller than the thickness of the sidewall of the insert section 22. Making use blind recesses or pocket holes instead of through openings also enhances and improves the mechanical stability and resistivity against mechanical loads present on the respective fastening element 25 during assembly. As a result a rather rigid, tight and long-term mechanically stable irreleasable connection of cartridge holder 20 and body 30 is provided.

The cartridge 50 comprises a reduced interior volume compared to standard sized cartridges or compared to a reference cartridge for which the drive mechanism 5 of the injection device 10 is originally configured and designed. Moreover, the ratio of dispensed volume versus axial displacement of the piston 52 of the cartridge 50 in distal direction 1 is substantially smaller than the corresponding ratio of a conventional injection device configured to set and to dispense doses of integer increments of IU.

In particular, the diameter of the tubular-shaped cartridge 50 is reduced compared to standard sized cartridges, e.g. providing a filling volume for the liquid medicament of 3 ml. For instance, the filling volume of the cartridge 50 according to the present disclosure is about 1.5 ml.

In order to accommodate and to fasten the cartridge 50 inside the housing 11 of the injection device 10 the cartridge holder 20 as shown in FIGS. 1-9 comprises at least three protrusions 120, 130 in an axial position distal from the flange section 23. The at least three protrusions 120, 130 extend radially outwardly from the outside surface 27 of a sleeve 29 forming or constituting a body of the cartridge holder 20. The flange section 23 divides the cartridge holder 20, in particular its sleeve 29 into a distal portion 29a and a proximal portion 29b. Distal and proximal portions 29a, 29b are separated by the flange section 23 having an annular shape and extending around the entire circumference of the sleeve 29.

As it is apparent from FIG. 2, the outer diameter of the sleeve 29 is reduced so that at least one or several radial gaps are formed between the outside surface 27 of the sidewall 26 of the sleeve 29 and an inside surface 48 of a protective cap 40 covering the distal portion 29a of the cartridge holder 20 when assembled thereto, as it is shown in FIGS. 6 and 12. In order to counteract an eventual clearance and loose fitting of the cap 40 to the cartridge holder 20 the at least three radially outwardly extending protrusions 120 serve to radially support the cap 40. As shown in FIG. 2, the radially outwardly located free ends of the three protrusions 120 exactly match with the shape or with the inner diameter of the inside face 48 of the cap 40. In this way, a mutual assembly of a conventional cap 40 with a diameter reduced cartridge holder 20 can be effectively provided.

Figure 9:
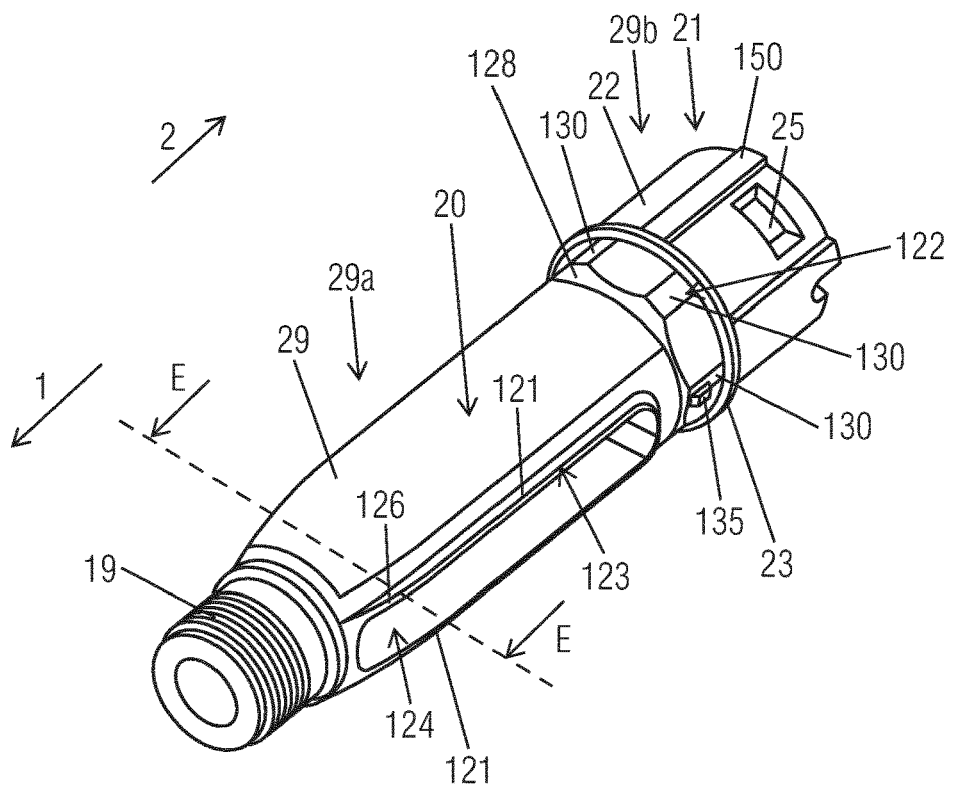
FIG. 9 is a perspective illustration of the cartridge holder according to FIGS. 1 to 8.

As it is shown in FIG. 9 and as further illustrated in the longitudinal cross-sections of FIGS. 5 and 7 the distal portion 29a of the sleeve 29 comprises a rather elongated window section 123 axially adjacent to a cap engaging section 122. The cap engaging section 122 comprises an outer diameter Dc that is larger than an outer diameter Dw of the window section 123. The inside surface 28 of the sleeve 29 may be substantially unaffected by this difference in diameter. The inside surface 28 may be strictly cylindrical or may comprise a somewhat conical narrowing structure towards the distal end of the cartridge holder 20. As shown in FIGS. 5, 7 and 9 the sidewall 26 of the sleeve 29 is somewhat thicker in the cap engaging section 122 than in the window section 123.

The radial widened cap engaging section 122 is further provided with two radially oppositely located and radially outwardly extending fastening elements 135 that are configured to engage with a correspondingly-shaped fastening structure 45 at an inside surface 48 of the cap 40. The fastening structure 45 is located at a proximal connecting end 41 of the cap 40 and is located on an inside facing surface portion of a somewhat cylindrically shaped sidewall 42 of the cap. As shown in FIG. 6, the fastening structure 45 of the cap 40 is complementary-shaped to the fastening elements 135 of the cap engaging section 122. The fastening elements 135 comprise radially outwardly extending knob like protrusions 136 to positively engage with a circumferential groove 46 on the inside of the cap 40 as shown in FIG. 6.

When the injection device 10 is fully assembled as shown in FIG. 12 a proximal end face of the cap 40 is in abutment with a distally facing surface of the flange section 26 and/or with a distal end face 34 of the body 30.

Figure 10:
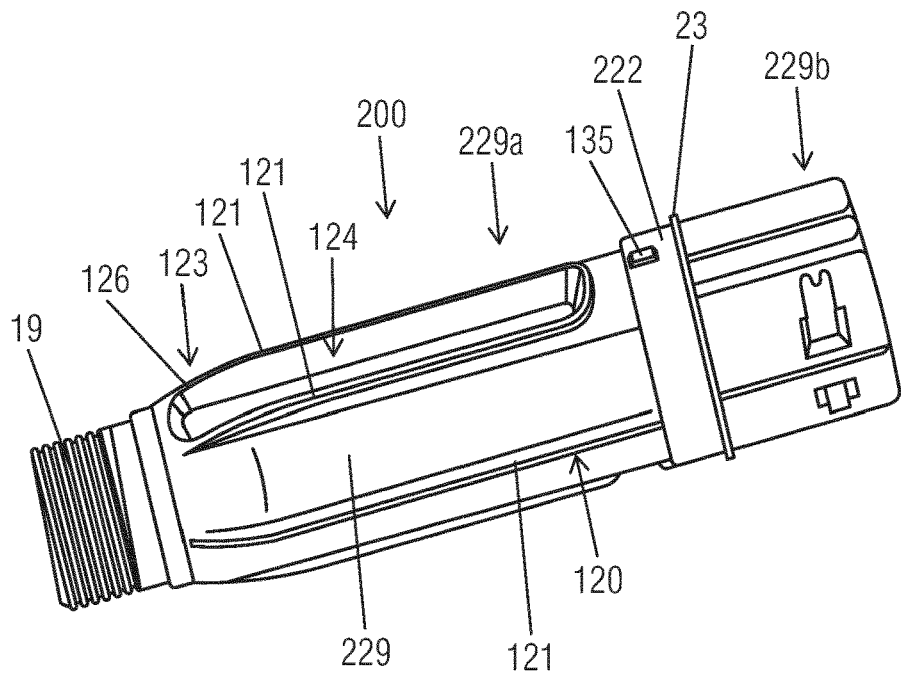
FIG. 10 is a perspective illustration of another embodiment of a cartridge holder.

The at least three protrusions 120 as shown in FIG. 9 or 10 are only provided in the window section 123 of the sleeve 29, 229. They comprise axially extending outer ribs 121 located on the outside surface 27 of the distal portion 29a, 229a of the sleeve 29, 229. All outer ribs 121 extend substantially parallel. As it is apparent from FIGS. 8 and 9 there are provided four elongated outer ribs 121 that extend almost over the entire axial elongation of the window section 123. Here, the outer ribs 121 extend along lateral side edges 125 of two through openings 124 provided in the sidewall 26 of the sleeve 29, 229.

In this way the outer ribs 121 not only serve to provide a radial support for the cap 40 but also provide structural stability to the window section 123 and to the through openings 124, which naturally represent a structural weakening of the sleeve 29, 229. In the embodiments as shown in FIGS. 8-10 there are provided two through openings 124 at radially opposite sections of the sleeve 29, 229. In this way, the sleeve 29, 229 does not necessarily have to be made of a transparent material. Visual inspection of a cartridge 50 located inside the sleeve 29, 229 is easily possible with the two radially oppositely arranged through openings 124.

As shown in FIG. 8, the outer ribs 121 are exclusively and only provided at the lateral side edges 125 of the two through openings 124. In this way, an upper and a lower region of the outside surface 27 of the sleeve 29 is free of any protrusions or recesses. Hence, a rather large semicircular or semi-cylindrical outside surface portion 27 is provided on which information regarding the medicament 53 or the injection device 10 could be provided, either by way of printing or by adhering a label to the outside surface 27 between two circumferentially adjacently arranged outer ribs 121.

As it is further apparent from FIG. 5 and FIG. 9, the outer ribs 121 comprise a beveled distal end 126. The beveled distal end 126 facilitates a smooth insertion of the cartridge holder 20, 200 into the cap 40. By way of beveled distal ends 126 of all outer ribs 121 a mutual radial centering of the cartridge holder 20, 200 and of the protective cap 40 can be provided when inserting the distal section 29a, 229a of the cartridge holder 20, 200 into the cap 40.

As it is further illustrated in FIGS. 1, 3, 4 and 8 there are also provided inner ribs 140 protruding radially inwardly from an inside surface 28 of the sleeve 29. The inner ribs 140 also extend in axial direction. As it is apparent from the longitudinal cross-section according to FIG. 7 the inner ribs 140 comprise a beveled proximal end 146. In the present embodiment there are provided altogether six inner ribs 140 along the inner circumference of the inside surface 28 of the sleeve 29. The inner ribs 140 are equidistantly spaced in circumferential or tangential direction so as to provide a radial support for the cartridge 50 arranged inside the sleeve 29.

By way of the radially inwardly extending inner ribs 140 any differences of an outer diameter of the diameter reduced cartridge 50 and an inner diameter of the sleeve 29 can be effectively compensated. By means of the beveled proximal ends 146 insertion of the cartridge 50 from a proximal end in distal direction 1 and into the hollow sleeve 29 can be facilitated. Also here a mutual radial centering and mutual radial displacement of the cartridge 50 relative to the sleeve 29 is obtained as the distal end of the cartridge 50 engages and slides along the beveled proximal ends 146 of the inner ribs 140. It can be further seen from FIG. 8 that four of the six inner ribs 140 extend along the lateral side edges 125 of the through openings 124 in the window section 123 of the sleeve 29. In this way, the lateral side edges 125 can be further structurally enhanced.

As it is further apparent from the cross-section according to FIG. 7 the outer diameter D1 of the distal portion 29a of the sleeve 29 is smaller than the outer diameter D2 of the proximal portion 29b of the sleeve 29. The cross-section according to FIG. 7 is somewhat exaggerated regarding the differences in diameters D1, D2 since the intersection runs through a radially outwardly extending rib 150 extending in axial direction on the outer circumference of the proximal portion 29b, 229b. This proximally located rib 150 matches with a correspondingly-shaped slot on the inside of the receptacle 32 of the body 30 so as to provide a rotational interlock of the cartridge holder 20, 200 and the body 30 as the proximal portion 29b, 229b, hence the insert section 22 of the cartridge holder 20, 200 is axially inserted into the receptacle 32 of the body 30.

Nevertheless the diameter D2 of the proximal portion 29b may be in the region or may be somewhat larger than the diameter D1 of the distal portion 29a in the region of the radially outwardly extending outer ribs 121.

As it is further shown in FIG. 7, the inner ribs 140 axially extend across the flange section 23. Hence, the inner ribs 140 extend from the proximal portion 29b towards the distal portion 29a of the sleeve 29. The radial height of the inner ribs 140 may constantly decrease towards the distal direction 1 so that the inner ribs 140 can provide a somewhat conical or tapered receiving or clamping structure for the cartridge 50, wherein said structure comprises an inner diameter near a distal end that is smaller than an inner diameter near a proximal end of the inner ribs 140.

In the two cross-sections of FIGS. 3 and 4 the cap engaging section 122 of the cartridge holder 20 is shown in two different axial positions. From a comparison of FIGS. 3 and 4 it is apparent, that the cap engaging section 122 comprises a polygonal-shaped outer cross-section. In the present embodiment the cap engaging section 122 comprises a hexagonal shape, wherein the corners or edges of the hexagon form or constitute radially outwardly extending protrusions 130. The radial outer end of these protrusions 130 substantially matches with the inside surface 48 of the cap 40. Hence, likewise the outer ribs 121, the protrusions 130 also provide a radial guiding of the cap 40.

In the cross-section according to FIG. 4 it is apparent, that the fastening elements 135, presently in form of radially outwardly extending protrusions 136 are located on an outer edge of the hexagonal-shaped cap engaging section 122. The polygonal-shaped outer cross-section with straight-shaped surface portions 127 may be further of particular benefit for a precise gripping and handling of the cartridge holder 20 in a fully automated mass manufacturing environment. As it is apparent from FIG. 1 the cap engaging section 122 axially adjoins into the flange section 23 in proximal direction 2. In distal direction 1 the radially widened or radially thickened cap engaging section 122 comprises a beveled edge 128 radially narrowing in distal direction 1.

The alternative embodiment according to FIG. 10 distinguishes from the embodiment as shown in FIGS. 1-9 in that the cap engaging section 222 is of substantially circular or rim-shaped geometry and comprises only two oppositely arranged and radially outwardly protruding fastening elements 135 to engage with the groove 46 of the cap 40. In addition, the cartridge holder 200 according to FIG. 10 comprises six radially outwardly protruding outer ribs 121, wherein two radially oppositely located outer ribs 121 are arranged circumferentially between the oppositely located through openings 124. As it is apparent from FIG. 10, those outer ribs 121 that lie outside the lateral side edges 125 of the through openings 124 extend in proximal direction 2 to adjoin the radially widened cap engaging section 222.

The cartridge holder 20, 200 as shown in the various Figures is typically manufactured as a single piece injection molded plastic component. Hence, all sections and portions of the cartridge holder 20, 200 as described above are integrally formed and are integrally integrated into the sleeve 29, 229 or into the respective cartridge holder 20, 200.

In FIGS. 11 and 12 the injection device 10 is illustrated comprising a drive mechanism 5 that has been commercially distributed over years and which is described in detail in the following documents: WO 2004/078239 A1, WO 2004/078240 A2 and WO 2004/078241 A1. The injection device 10 is of disposable type. Hence, when the medicament 53 contained in the cartridge 50 has been dispensed or used up the entire device 10 is intended to be discarded. Therefore, the cartridge holder 20 to accommodate the cartridge 50 is irreleasably connectable to the proximal housing component, hence to the body 30. A cap 40 to cover the cartridge holder 20 extending distally from the body 30 is releasably interconnectable with the cartridge holder 20.

The drive mechanism 5 comprises numerous mechanically interacting components. The flange like support 36 of the body 30 comprises a threaded through opening 37 threadedly engaged with a distal thread 112 of the piston rod 110. The distal end of the piston rod 110 comprises a bearing 115 on which a pressure foot 116 is free to rotate with the longitudinal axis of the piston rod 110 as an axis of rotation. The pressure foot 116 is configured to axially abut against the proximally facing thrust receiving surface of the piston 52 of the cartridge 50. During a dispensing action the piston rod 110 rotates relative to the body 30 thereby experiencing a distally directed advancing motion relative to the body 30 and hence relative to the barrel 51 of the cartridge 50. As a consequence, the piston 52 of the cartridge 50 is displaced in distal direction by a well-defined distance due to the threaded engagement of the piston rod 110 with the body 30.

The piston rod 110 is further provided with a second thread 114 at its proximal end. The distal thread 112 and the proximal thread 114 are oppositely handed.

There is further provided a drive sleeve 100 having a hollow interior to receive the piston rod 20. The drive sleeve 100 comprises an inner thread threadedly engaged with the proximal thread 114 of the piston rod 110. Moreover, the drive sleeve 100 comprises an outer threaded section 105 at its distal end. The threaded section is axially confined between a distal flange portion 102 and another flange portion 104 located at a predefined axial distance from the distal flange portion 102. Between the two flange portions 102, 104 there is provided a last dose limiting member 106 in form of a semi-circular nut having an internal thread matching the threaded section 105 of the drive sleeve 100.

The last dose limiting member 106 further comprises a radial recess or protrusion at its outer circumference to engage with a complementary-shaped recess or protrusion at an inside of the sidewall 33 of the body 30. In this way the last dose limiting member 106 is splined to the body 30. A rotation of the drive sleeve 100 in a dose incrementing or clockwise direction during consecutive dose setting procedures leads to an accumulative axial displacement of the last dose limiting member 106 relative to the drive sleeve 100. There is further provided an annular spring 96 that is in axial abutment with a proximally facing surface of the flange portion 104. Moreover, there is provided a tubular-shaped clutch member 90. At a first end the clutch member 90 is provided with a series of circumferentially directed saw teeth. Towards a second opposite end of the clutch member 90 there is located a radially inwardly directed flange.

Furthermore, there is provided a dose dial or dose indicating sleeve 80. The dose indicating sleeve 80 is provided outside of the spring 96 and the clutch member 90 and is located radially inward of the body 30. A helical groove 81 is provided about an outer surface of the dose indicating sleeve 80. The body 30 is provided with a window 44 through which a part of the outer surface of the dose indicating sleeve 80 can be seen. The body 30 is further provided with a helical rib at an inside sidewall portion of an insert piece 70, which helical rib is to be seated in the helical groove 81 of the dose indicating sleeve 80. The tubular shaped insert piece 70 is inserted into the proximal end of the body 30. It is rotationally and axially fixed to the body 30. There are provided first and second stops on the body 30 to limit a dose setting procedure during which the dose indicating sleeve 80 is rotated in a helical motion relative to the body 30.

A dose dial grip 66 is disposed about an outer surface of the proximal end of the dose indicating sleeve 80. An outer diameter of the dose dial 66 typically corresponds to the outer diameter of the body 30. The dose dial 66 is secured to the dose indicating sleeve 80 to prevent relative movement therebetween. The dose dial 66 is provided with a central opening.

Furthermore, a dose button 60 of generally T-shape is provided at a proximal end of the injection device 10. A stem 62 of the dose button 60 extends through the opening in the dose dial 66 through an inner diameter of extensions of the drive sleeve 100 and into a receiving recess at the proximal end of the piston rod 110. The stem 62 is retained for limited axial movement in the drive sleeve 100 and against rotation with respect thereto. A head 64 of the dose button 60 is generally circular. A skirt extends from a periphery of the head 64 and is further adapted to be seated in a proximally accessible annular recess of the dose dial 66.

To dial a dose a user rotates the dose dial 66. With the spring 96 also acting as a clicker and the clutch member 90 engaged, the drive sleeve 100 the spring or clicker 96, the clutch member 90 and the dose indicating sleeve 80 rotate with the dose dial 66. Audible and tactile feedback of the dose being dialed is provided by the spring 96 and by the clutch member 90. Torque is transmitted through saw teeth between the spring 96 and the clutch member 90. The helical groove 81 on the dose indicating sleeve 80 and a helical groove in the drive sleeve 100 have the same lead. This allows the dose indicating sleeve 80 to extend from the body 30 and the drive sleeve 100 to climb the piston rod 110 at the same rate. At a limit of travel a radial stop on the dose indicating sleeve 80 engages either with a first stop or a second stop provided on the body 30 to prevent further movement. Rotation of the piston rod 110 is prevented due to the opposing directions of the overall and driven threads on the piston rod 110.

The last dose limiting member 106 keyed to the body is advanced along the threaded section 105 by the rotation of the drive sleeve 100. When a final dose dispensed position is reached, a radial stop formed on a surface of the last dose limiting member 106 abuts a radial stop on the flange portion 104 of the drive sleeve 100, preventing both, the last dose limiting member 106 and the drive sleeve 100 from rotating further.

Should a user inadvertently dial beyond the desired dosage, the pen-injector 10 allows the dosage to be dialed down without dispense of the medicament from the cartridge 50. For this the dose dial 66 is simply counter-rotated. This causes the system to act in reverse. A flexible arm of the spring or clicker 96 then acts as a ratchet preventing the spring 96 from rotating. The torque transmitted through the clutch member 90 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the dose button 60. This displaces the clutch member 90 axially with respect to the dose indicating sleeve 80 causing dog teeth thereof to disengage. However, the clutch member 90 remains keyed in rotation to the drive sleeve 100. The dose indicating sleeve 80 and the dose dial 66 are now free to rotate in accordance with the helical groove 81.

The axial movement deforms the flexible arm of the spring 96 to ensure the saw teeth cannot be overhauled during dispense. This prevents the drive sleeve 100 from rotating with respect to the body 30 though it is still free to move axially with respect thereto. The deformation is subsequently used to urge the spring 96 and the clutch member 90 back along the drive sleeve 100 to restore the connection between the clutch member 90 and the dose indicating sleeve 80 when the distally directed dispensing pressure is removed from the dose button 60.

The longitudinal axial movement of the drive sleeve 100 causes the piston rod 110 to rotate through the through opening 37 of the support 36 of the body, thereby to advance the piston 52 in the cartridge 50. Once the dialed dose has been dispensed, the dose indicating sleeve 80 is prevented from further rotation by contact of a plurality of members extending from the dose dial 66 with a corresponding plurality of stops. A zero dose position is finally determined by the abutment of one of axially extending edges of members of the dose indicating sleeve 80 with a corresponding stop of the body 30.

The drive mechanism 5 as described above is only exemplary for one of a plurality of differently configured drive mechanisms that are generally implementable in a disposable pen-injector. Hence, the interface and interconnection of housing components, such like the cartridge holder 20 and the body 30 as explained above can be generally implemented with a large variety of different drive mechanisms.

LIST OF REFERENCE NUMBERS 1 distal direction
2 proximal direction
5 drive mechanism
6 axial interlock
10 injection device
11 housing
19 threaded socket
20 cartridge holder
21 proximal connecting end
22 insert section
23 flange section
24 abutment face
25 fastening element
26 sidewall
27 outside surface
28 inside surface
29 sleeve
29a distal portion
29b proximal portion
30 body
31 distal connecting end
32 receptacle
33 sidewall
34 end face
35 fastening element
35a beveled section
36 support
37 through opening
38 beveled edge
40 cap
41 proximal connecting end
42 sidewall
44 window
45 fastening structure
46 groove
48 inside surface
50 cartridge
51 barrel
52 piston
53 medicament
54 seal
60 dose button
62 stem
64 head
66 dose dial
70 insert piece
80 dose indicating sleeve
81 helical groove
90 clutch member
96 spring
100 drive sleeve
102 distal flange portion
104 flange portion
105 threaded section
106 last dose limiting member
110 piston rod
112 distal thread
114 proximal thread
115 bearing
116 pressure foot
120 protrusion
121 outer rib
122 cap engaging section
123 window section
124 through opening
125 side edge
126 beveled distal end
127 surface portion
128 beveled edge
130 protrusion
135 fastening element
136 protrusion
140 inner rib
146 beveled proximal end
150 rib
200 cartridge holder
222 cap engaging section
229a distal portion

The invention claimed is:
1. A cartridge holder of an injection device comprising:
a tubular shaped elongated sleeve extending in an axial direction to accommodate a cartridge filled with a medicament, the cartridge comprising a tubular shaped barrel portion, wherein the sleeve comprises:

a proximal connecting end configured to connect with a distal connecting end of a body of the injection device, wherein the body is configured to accommodate a drive mechanism of the injection device, wherein the drive mechanism is operably engageable with a piston of the cartridge;

a flange section extending radially outwardly from an outside surface of the sleeve and having a proximally facing abutment face to axially abut with a distal end face of the distal connecting end of the body;

a distal portion of the sleeve located distally from the flange section and shaped to accommodate the tubular shaped barrel portion of the cartridge, the distal portion of the sleeve comprising an outer diameter that is smaller than an outer diameter of a proximal portion of the sleeve, the proximal portion of the sleeve being located proximally from the flange section; and at least three protrusions located on the outside surface of the distal portion of the sleeve, each protrusion of the at least three protrusions extending radially outwardly from the outside surface of the sleeve and being distributed around a circumference of the sleeve;

wherein at least one of the at least three protrusions comprises an elongated axially extending outer rib on the outside surface of the distal portion of the sleeve;

wherein radially outwardly located ends of the at least three protrusions of the sleeve match with an inner diameter of a cap configured and shaped to cover at least a portion of the sleeve of the cartridge holder.

2. The cartridge holder according to claim 1, wherein the distal portion of the sleeve comprises a cap engaging section and a window section, wherein the cap engaging section is axially located between the window section and the flange section.

3. The cartridge holder according to claim 2, wherein the cap engaging section comprises an outer diameter that is larger than an outer diameter of the window section.

4. The cartridge holder according to claim 2, wherein the window section comprises at least one through opening in a sidewall of the sleeve.

5. The cartridge holder according to claim 4, wherein the sleeve comprises at least three axially extending inner ribs protruding radially inwardly from an inside surface of the sleeve and being distributed around an inner circumference of the sleeve.

6. The cartridge holder according to claim 5, wherein at least one of the at least three axially extending inner ribs extends along a lateral side edge of the at least one through opening.

7. The cartridge holder according to claim 6, wherein at least one of the at least three axially extending inner ribs comprises a beveled proximal end.

8. The cartridge holder according to claim 7, wherein the cap engaging section comprises at least two fastening elements configured to releasably and to positively engage with at least one complementary shaped fastening structure at an inside surface of the cap configured to cover the sleeve.

9. The cartridge holder according to claim 8, wherein the cap engaging section comprises the at least three protrusions extending radially outwardly and adjoining the flange section in the axial direction and being distributed around a circumference of the cap engaging section.

10. The cartridge holder according to claim 9, wherein the cap engaging section comprises a polygonal shaped outer cross section and wherein the at least three protrusions extending radially outwardly are located in corners of a polygon.

11. The cartridge holder according to claim 4, wherein the elongated axially extending outer rib extends along a lateral side edge of the at least one through opening.

12. The cartridge holder according to claim 1, wherein the elongated axially extending outer rib comprises a beveled distal end.

13. A cartridge holder assembly comprising:
a cartridge holder comprising:
a tubular shaped elongated sleeve extending in an axial direction to accommodate a cartridge filled with a medicament, the cartridge comprising a tubular shaped barrel portion, wherein the sleeve comprises:
a proximal connecting end configured to connect with a distal connecting end of a body of an injection device, wherein the body is configured to accommodate a drive mechanism of the injection device, wherein the drive mechanism is operably engageable with a piston of the cartridge;
a flange section extending radially outwardly from an outside surface of the sleeve and having a proximally facing abutment face to axially abut with a distal end face of the distal connecting end of the body;
a distal portion of the sleeve located distally from the flange section and being shaped to accommodate the tubular shaped barrel portion of the cartridge, the distal portion of the sleeve comprising an outer diameter that is smaller than an outer diameter of the proximal connecting end; and
at least three protrusions located on the outside surface of the distal portion of the sleeve, each protrusion of the at least three protrusions extending radially outwardly from the outside surface of the sleeve and being distributed around a circumference of the sleeve;
wherein at least one of the at least three protrusions comprises an elongated axially extending outer rib on the outside surface of the distal portion of the sleeve; and
a cap to cover at least a portion of the sleeve of the cartridge holder, wherein radially outwardly located ends of the at least three protrusions of the sleeve match with an inner diameter of the cap.

14. An injection device for administering a liquid medicament, the injection device comprises:
a cartridge holder;
a cartridge filled with a liquid medicament and comprising a tubular shaped barrel portion, the cartridge accommodated in the cartridge holder, the cartridge comprising a piston axially displaceably arranged therein;
a body connected to the cartridge holder and configured to accommodate a drive mechanism operably engageable with the piston of the cartridge;
the cartridge holder comprising:
a tubular shaped elongated sleeve extending in an axial direction, wherein the sleeve comprises:
a proximal connecting end configured to connect with a distal connecting end of the body of the injection device;
a flange section extending radially outwardly from an outside surface of the sleeve and having a proximally facing abutment face to axially abut with a distal end face of the distal connecting end of the body;

a distal portion of the sleeve located distally from the flange section and being shaped to accommodate the tubular shaped barrel portion of the cartridge, the distal portion of the sleeve comprising an outer diameter that is smaller than an outer diameter of the proximal connecting end; and at least three protrusions located on the outside surface of the distal portion of the sleeve, each protrusion of the at least three protrusions extending radially outwardly from the outside surface of the sleeve and being distributed around a circumference of the sleeve;

wherein at least one of the at least three protrusions comprises an elongated axially extending outer rib on the outside surface of the distal portion of the sleeve; and a cap to cover at least a portion of the sleeve of the cartridge holder, wherein radially outwardly located ends of the at least three protrusions of the sleeve match with an inner diameter of the cap.

\* \* \* \* \*